(12) United States Patent
Hathaway et al.

(10) Patent No.: US 10,048,056 B2
(45) Date of Patent: Aug. 14, 2018

(54) DISPERSION COMPENSATION

(71) Applicant: Cellview Imaging Inc., Toronto (CA)

(72) Inventors: Mark Hathaway, Canterbury (GB); Rishard Weitz, Toronto (CA)

(73) Assignee: Cellview Imaging Inc. (CA)

( * ) Notice: Subject to any disclaimer, the term of this patent is extended or adjusted under 35 U.S.C. 154(b) by 32 days.

(21) Appl. No.: 15/318,234

(22) PCT Filed: Jun. 11, 2015

(86) PCT No.: PCT/CA2015/000375
§ 371 (c)(1),
(2) Date: Dec. 12, 2016

(87) PCT Pub. No.: WO2015/188258
PCT Pub. Date: Dec. 17, 2015

(65) Prior Publication Data
US 2017/0108328 A1  Apr. 20, 2017

Related U.S. Application Data

(60) Provisional application No. 62/010,643, filed on Jun. 11, 2014.

(51) Int. Cl.
*G01B 9/02* (2006.01)
*A61B 3/10* (2006.01)

(52) U.S. Cl.
CPC .......... *G01B 9/02058* (2013.01); *A61B 3/102* (2013.01); *G01B 9/02091* (2013.01)

(58) Field of Classification Search
CPC .. G01B 9/02058; G01B 9/02091; A61B 3/102
See application file for complete search history.

(56) References Cited

U.S. PATENT DOCUMENTS 7,719,692 B2    5/2010  Izatt et al.
8,705,041 B2 *  4/2014  Eckman ............ G02B 21/0004
                                                        356/450

(Continued)

FOREIGN PATENT DOCUMENTS

CN    100464696 C     3/2009
CN    100493444 C     6/2009
WO    2012123122 A1   9/2012

OTHER PUBLICATIONS

Hofer, Bernd et al. "Dispersion encoded full range frequency domain optical coherence tomography". Optics Express, vol. 17, No. 1, Jan. 5, 2009, pp. 7-24.*

(Continued)

*Primary Examiner* — Michael A Lyons
(74) *Attorney, Agent, or Firm* — Laubscher, Spendlove & Laubscher, P.C.

(57) ABSTRACT

In a OCT interferometer it is necessary to balance dispersion within the reference arm with dispersion within the object arm. This is normally done by replicating within the reference arm the components found in the object arm. This adds to the complexity and cost of the OCT interferometer. A method is provided for determining the design of and designing a simplified OCT interferometer, in which the reference arm contains only a single piece of glass of a single glass type. This reduces the cost and complexity of the OCT interferometer, and reduces power loss and undesired reflections within the reference arm.

9 Claims, 3 Drawing Sheets

(56) References Cited

U.S. PATENT DOCUMENTS

| | | | |
|---|---|---|---|
| 9,696,136 B2 * | 7/2017 | Wang | G01B 9/02091 |
| 9,867,536 B2 * | 1/2018 | Izatt | A61B 3/102 |
| 2003/0004412 A1 | 1/2003 | Izatt et al. | |
| 2003/0048532 A1 * | 3/2003 | Lindner | G02B 13/06 |
| | | | 359/511 |
| 2005/0259265 A1 | 11/2005 | Delega | |

OTHER PUBLICATIONS

Wojtkowski, Maciej et al. "Ultrahigh-resolution, high-speed, Fourier domain optical coherence tomography and methods for dispersion compensation". Optics Express, vol. 12, No. 11, May 31, 2004, pp. 2404-2422.*

Drexler, W., et al, In vivo ultrahigh-resolution optical coherence tomography, Optics Letters, 1999, pp. 1221-1223, vol. 24, No. 17, Optical Society of America.

* cited by examiner

DISPERSION COMPENSATION

FIELD OF INVENTION

This invention relates to balancing dispersion in broadband interferometers.

BACKGROUND

In optical coherence tomography (OCT), the longitudinal resolution in an A-scan depends partly on the degree of similarity between dispersion in a reference arm and dispersion in an object arm. Dispersion is the term given when the propagation constant of a wave has a nonlinear dependence on frequency. The zero-th derivative of the phase function of the wave with respect to the frequency indicates the phase delay, the first derivative indicates the group delay, and the second derivative indicates the group delay dispersion.

Generally the dispersive properties of a component will be known and the problem is to determine what effect this will have on a time varying signal. In interferometers the effect is well known and the problem then is to balance the dispersion in each arm.

A dispersion imbalance in broadband interferometers causes a reduction of signal-to-noise and a broadening of the coherence profile, which in turn means a reduction in longitudinal resolution in an OCT A-scan. The presence of dispersive elements in the interferometer is not in itself the issue, but the dispersion in both arms of the interferometer must be balanced to achieve optimal signal-to-noise and resolution. Generally this is achieved by duplicating any element located in the object arm within the reference arm. For example, lenses are usually made up of different glass types or various thicknesses, and there are generally more in the object arm than in the reference arm. Each element within each arm may contribute to dispersion of the light within the arm, generally in different ways. A common technique therefore is to include extra pieces of glass in the reference path, matching the glass types and mean thicknesses in each lens in the object path, to compensate for the additional dispersion present in the object path. Each glass type is usually bonded together to form a compound rod which is included in the reference path. While this technique does ensure the mean dispersion in each arm of the interferometer is well matched, the cost and complexity of the interferometer are increased. In addition, there is an increase in multiple reflections due to boundaries between different materials and power loss.

There is a need to provide a system which equalized the dispersion in the arms of an interferometer without the cost and complexity of reproducing each functional element located in the object arm within the reference arm.

SUMMARY

By using a single glass type with a given thickness within the reference arm in order to mimic the dispersion characteristics of various elements within the object arm, the design of an OCT interferometer can be greatly simplified.

BRIEF DESCRIPTION OF THE DRAWINGS

The features and advantages of embodiments of the invention will become more apparent from the following detailed description of the preferred embodiment(s) with reference to the attached figures, wherein.

It is noted that in the attached figures, like features bear similar labels.

DETAILED DESCRIPTION OF THE PREFERRED EMBODIMENTS

OCT interferometers contain various glass components, such as lenses, with varying physical properties, and generally the phase function $\phi(\omega)$ is highly nonlinear. However for relatively narrow band sources (typical of OCT systems) and for frequencies far from an absorption edge (typically found in the ultraviolet for most glasses) the phase function can be accurately approximated by a Taylor series expansion:

$$\phi(\omega) \approx \phi_0 + (\omega - \omega_0) \cdot \phi_1 + (\omega - \omega_0)^2 \cdot \frac{\phi_2}{2} + \ldots + (\omega - \omega_0)^n \cdot \frac{\phi_n}{n!}$$

$$\text{where } \phi_n = \frac{d^n \phi}{d\omega^n}\bigg|_{\omega=\omega_0}$$

and $\omega_0$ is the center frequency of the light source.

Given these conditions only terms up to second order are required, i.e. up to $\phi_2$. In bulk materials the phase function after propagation through a thickness of glass given by x, is related to the propagation constant of the material $\beta$ such that:

$$\phi(\omega) = \beta(\omega) \cdot x,$$

and therefore after expansion:

$$\phi_n = \frac{d^n \phi}{d\omega^n}\bigg|_{\omega=\omega_0} = x \cdot \frac{d^n \beta}{d\omega^n}\bigg|_{\omega=\omega_0} = x \cdot \beta_n.$$

For propagation in a vacuum, to which propagation in air is a good approximation, the dependence of $\beta$ on $\omega$ is known explicitly:

$$\beta(\omega) = k(\omega) = \frac{\omega}{c}$$

The values of $\beta_n$ in a vacuum are found by differentiation to be:

$$\beta_0 = k_0 = \frac{\omega_0}{c}, \beta_1 = \frac{1}{c}, \beta_2 = 0.$$

So far only a distributed form of dispersion, in which the phase shifts caused by propagation are directly proportional to the distance travelled, has been considered. There are also cases where the phase shifts can occur over very small regions of space. The use of dielectric coatings to produce mirrors, beam splitters and anti-reflection coatings are examples. The dispersive properties of these devices are dominated by their structure rather than the materials used to make them. These devices are best described by the total phase shift, $\phi(\omega)$, that they induce after transmission or reflection of the input signal, in which case the previous derivations for $\phi(\omega)$ can still be used.

Figure 1:
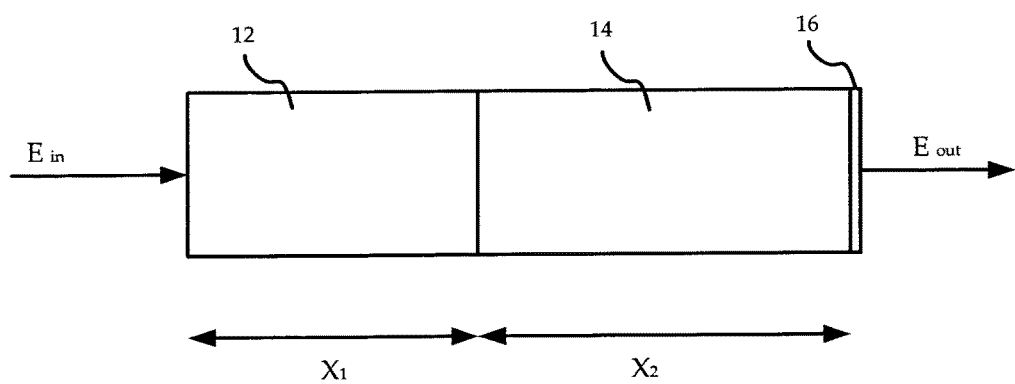
FIG. 1 shows a hypothetical optical pathway.

In a more complicated system made up from several elements, all that needs to be calculated is the total phase shift after passing through the system. Referring to FIG. 1, a hypothetical optical pathway is shown. The optical pathway shown is merely a hypothetical example of an optical pathway, and is intended to show how the invention works. The optical pathway shown in FIG. 1 comprises a first material 12 with a length $x_1$, a second material 14 with a length $x_2$, and a coating 16. The total phase shift can be written as:

$$\phi_T(\omega) = \phi_1(\omega) + \phi_2(\omega) + \phi_3(\omega)$$
$$= \beta_1(\omega) \cdot x_1 + \beta_2(\omega) \cdot x_2 + \phi_3(\omega)$$

where here the subscript T refers to the total phase shift and the subscripts 1, 2, and 3 refer to the first material 12, the second material 14, and the coating 16 respectively. Expanding each term as a Taylor series leads to expressions for the phase delay, group delay and GDD:

$$\phi_{T0} = \beta_{10} \cdot x_1 + \beta_{20} \cdot x_2 + \phi_{30} = \text{Total Phase Delay}$$

$$\phi_{T1} = \beta_{11} \cdot x_1 + \beta_{21} \cdot x_2 + \phi_{31} = \text{Total Group Delay}$$

$$\phi_{T2} = \beta_{12} \cdot x_1 + \beta_{22} \cdot x_2 + \phi_{32} = \text{Total GDD}$$

where the notation $AF_{ij}$ represents the $j^{th}$ derivative with respect to frequency for the $i^{th}$ material.

To balance dispersion within the arms of an interferometer the phase function $\phi(\omega)$ in each arm must be equal. However some simplifications can be made. In OCT the signal is always produced by generating a carrier, either by sweeping the path length or in spectral OCT by sweeping across the frequency spectrum of the source. In either case this means the constant phase term $\phi_0$ in each arm can be ignored, and only the second and third terms $\phi_1$ and $\phi_2$ must be balanced for the reference and object arms.

Figure 2:
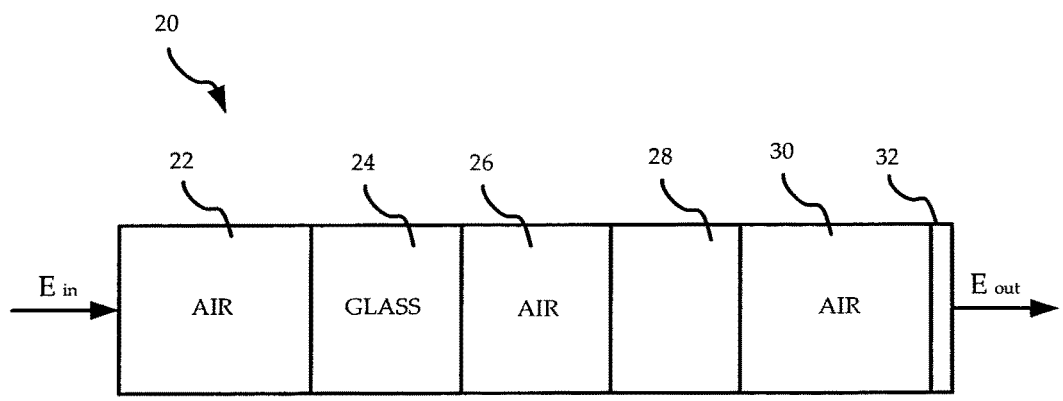
FIG. 2 shows a diagram of an example reference arm of an interferometer according to one embodiment of the invention.

Referring to FIG. 2, a diagram of an example reference arm used in an interferometer is shown according to one embodiment of the invention. The reference arm 20 includes a first air portion 22, a glass portion 24 with a length $x_{glass}$ and composed of glass of a single glass type, a second air portion 26, a bulk component 28, a third air portion 30, and a discrete component 32.

The bulk component is a component necessary to produce an output signal from the reference arm, such as a lens which collimates the light within the reference arm. The discrete component is a component necessary to produce an output signal from the reference arm, such as a mirror which reflects light reaching the end of the reference arm. More generally, there are zero or more bulk components and one or more discrete components. These components are the optical components within the reference arm necessary for the reference arm to produce an output signal. They are not components added merely to compensate for dispersion within the object arm.

Figure 3:
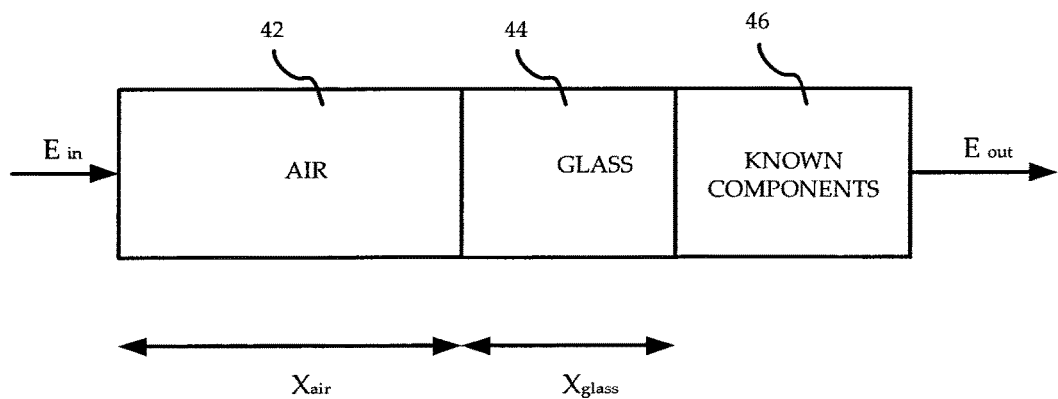
FIG. 3 shows a schematic representation of a reference arm of an interferometer according to one embodiment of the invention.

The dispersions in the segments of the reference arm are additive. Therefore the bulk component(s) and the discrete components can be considered as a single known component for the purposes of dispersion. Similarly, the various air portions can be considered as a single air portion for the purposes of dispersion. Referring to FIG. 3, a schematic representation of a reference arm used in OCT is shown according to one embodiment of the invention. The schematic representation 40 of the reference arm includes an air portion 42 with a length $x_{air}$, a glass portion 44 with a length $x_{glass}$ of a single glass type, and a known components portion 46. The known components portion 46 represents at least one necessary and known optical component present in the reference arm. The at least one necessary and known optical component is necessary in order for the reference arm to produce an output signal, and is not present merely to compensate for dispersion in the object arm.

The schematic representation of a reference arm shown in FIG. 3 can be used to represent the example reference arm shown in FIG. 2. Because dispersion is additive, the various air portions 22, 26, and 30 of FIG. 2 can be represented as a single air portion 42 in FIG. 3 whose length $x_{air}$ is equal to the sum of the lengths of the individual air portions in FIG. 2. The glass portion 24 of FIG. 2 is represented simply by an identical glass portion 44. The various known components 28 and 32 can be represented as a single known components portion 46. The dispersion $\Phi_{known}$ of the known components portion 46 is equal to the sum of the dispersions of the known components, i.e.

$$\Phi_{known} = \Sigma \Phi_{component}$$

where $\Phi_{component}$ is the dispersion of a particular optical component.

The total group delay for light passing through the reference arm is the sum of the group delay through each portion. The total group delay in the reference arm is therefore $$\Phi_{ref,1} = x_{air} \cdot \beta_{air,1} + x_{glass} \cdot \beta_{glass,1} + \Phi_{known,1},$$

and since the dispersion of light passing through air is effectively the same as the dispersion of light passing through a vacuum, this simplifies to $$\Phi_{ref,1} = x_{air}/c + x_{glass} \cdot \beta_{glass,1} + \Phi_{known,1},$$

Similarly, the total GDD in the reference arm becomes $$\Phi_{ref,2} = x_{glass} \cdot \beta_{glass,2} + \Phi_{known,2}.$$

Broadly, in producing a reference arm within an interferometer, the group delay and the group dispersion delay (GDD) of an object arm of the interferometer are determined. The GDD of the object arm is matched with the GDD of a hypothetical reference arm comprising an air portion, a glass portion comprising glass of a single glass type, and a known components portion. The glass type and the length of the glass portion is determined from the matching of the GDDs. In addition, the group delay of the object arm is matched with the group delay of the hypothetical reference arm. The length of the air portion is determined from the matching of the group delays, the glass type, and the length of the glass portion. A real reference arm can then be produced having an air portion and a glass portion each having the same properties as the air portion and the glass portion of the hypothetical reference arm.

Figure 4:
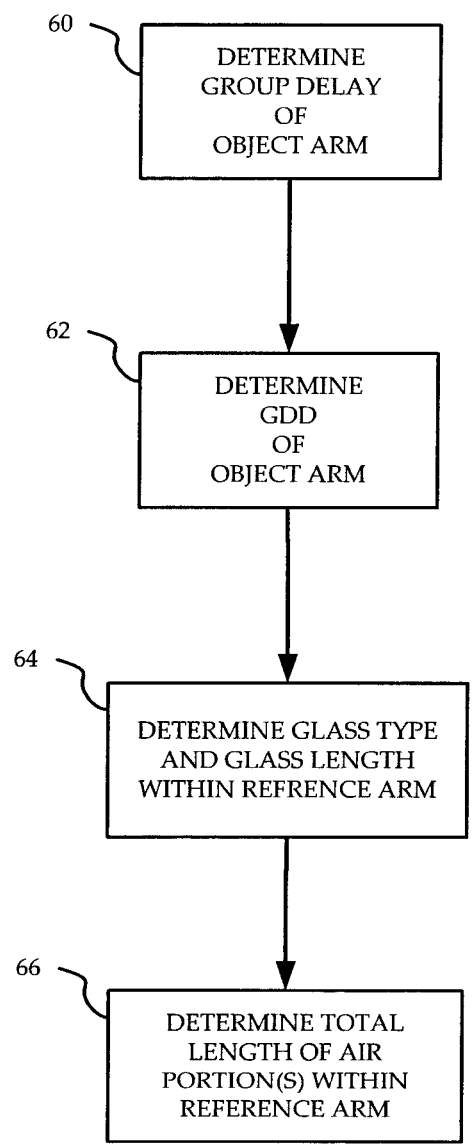
FIG. 4 shows a flowchart of a method by which the reference arm of an OCT interferometer is designed according to one embodiment of the invention.

Referring to FIG. 4, a flowchart of a method by which a reference arm is produced according to one embodiment of the invention is shown. At step 60 the total group delay of the object arm, $\Phi_{obj,1}$ is determined. As explained above, the total group delay is the sum of the group delays of the components within the object arm. The components within the object arm are known once the design of the object arm is complete, including their respective glass types and thicknesses. The total dispersion of the object arm can then be determined by referring to dispersion data for each glass type, although other methods of determining the total dispersion of the object arm can be used such as by using a modelling package. In one embodiment the additional dispersion from a patient's eye is included in the total dispersion of the object arm, for example by using the dispersion properties of water.

At step 62 the total GDD of the object arm, $\Phi_{obj,2}$, is determined. The GDD is determined in the same way as is the total group delay, i.e. by adding the dispersive contribution of each component within the object arm, including possibly the eye. Of course the precise order of these two determinations is not important and they could in fact be determined simultaneously.

At step 64 the glass type and the length $X_{glass}$ of the glass portion 44 are determined by requiring that the dispersion in the reference arm is the same as the dispersion in the object arm, as desired in an OCT interferometer. Setting the GDD in each arm to be the same, $$x_{glass} \cdot \beta_{glass,2} + \Phi_{known,2} = \Phi_{obj,2}.$$

Since the GDD of the object arm was determined at step 62 and the GDD $\Phi_{known,2}$ of known components within the reference arm is known, a glass type can be chosen such that the above equality is satisfied while still giving a length $x_{glass}$ of the glass portion 44 that is practical for an OCT interferometer. Once the glass type and length $x_{glass}$ of the glass portion 44 are determined, then at step 66 the length $x_{air}$ of the air portion 42 is determined by setting the group delay in each arm to be the same:

$$x_{air}/c + x_{glass} \cdot \beta_{glass,1} + \Phi_{known,1} = \Phi_{obj,1}.$$

Since the glass type of the glass portion 44, and hence $\beta_{glass,1}$, the length $x_{glass}$, the group delay $\Phi_{obj,1}$ within the object arm, and the group delay $\Phi_{known,1}$ of known and necessary components within the reference arm are known, the length $x_{air}$ of the air portion 42 can be determined. Of course if the total length of $x_{air}$ and $x_{glass}$ would not result in a practical length for the reference arm of an OCT interferometer, then a different glass type of the glass portion 44 can be used.

Once the glass type, the length of the glass portion, and the total length of the air portion or air portions are determined, a reference arm for use in an OCT interferometer can be built having these properties. The length of any one or more of the air portion or air portions can be set so that the total length of the air portion or air portions is equal to that determined total air portion length $x_{air}$. Similarly an OCT interferometer having such a reference arm can be built.

The invention has been described with reference to an OCT interferometer. More generally, the invention may be used to provide the reference arm of any interferometer.

The invention has been described as placing a single glass portion of determined length and type in the reference arm of an OCT interferometer in order to compensate for differences in dispersion between the object arm and the reference arm of the OCT interferometer. Alternatively, a single glass can be placed in the object arm in order to compensate for such differences if the dispersion in the reference arm would otherwise be higher than that in the object arm, the length and type of glass being determined as described above.

The embodiments presented are exemplary only and persons skilled in the art would appreciate that variations to the embodiments described above may be made without departing from the spirit of the invention. The scope of the invention is solely defined by the appended claims.

We claim:

1. A method of producing a reference arm within an interferometer, comprising:
   determining the group delay and the group dispersion delay (GDD) of an object arm of the interferometer;
   determining the dispersion of known components within the reference arm, the known components being necessary for production of an output signal from the reference arm when in use;
   matching the GDD of the object arm with the GDD of a hypothetical reference arm comprising an air portion, a glass portion comprising glass of a single glass type, and a known components portion having a dispersion equal to the dispersion of the known components;
   determining the glass type and the length of the glass portion from the matching of the GDDs;
   matching the group delay of the object arm with the group delay of the hypothetical reference arm;
   determining the total length of the air portion from the matching of the group delays, the glass type, and the length of the glass portion; and
   producing a real reference arm, whose sum of the lengths of at least one air portion within the reference arm is equal to the total length of the air portion of the hypothetical reference arm, and having a glass portion having the same properties as the glass portion of the hypothetical reference arm.

2. The method of claim 1 wherein matching the GDD of the object arm with the GDD of the hypothetical reference arm comprises setting $$x_{glass} \cdot \beta_{glass,2} + \Phi_{known,2} = \Phi_{obj,2},$$

where $x_{glass}$ is the length of the glass portion, $\beta_{glass,2}$ is the second derivative of the propagation constant of the glass portion with respect to frequency, $\Phi_{known,2}$ is the GDD of the known components portion, and $\Phi_{obj,2}$ is the GDD of the object arm, and wherein matching the group delay of the object arm with the group delay of the hypothetical reference arm comprises setting $$x_{air}/c + x_{glass} \cdot \beta_{glass,1} + \Phi_{known,1} = \Phi_{obj,1},$$

where $x_{air}$ is the length of the air portion, c is the speed of light in a vacuum, $\beta_{glass,1}$ is the first derivative of the propagation constant of the glass portion with respect to frequency, $\Phi_{known,1}$ is the group delay of the known components portion, and $\Phi_{obj,1}$ is the group delay of the object arm.

3. The method of claim 1 wherein the glass type is determined such that the real reference arm can be used in an optical coherence tomography interferometer.

4. The method of claim 1 wherein the group delay and the GDD of the object arm include the group delay and the GDD of a hypothetical patient eye.

5. A reference arm of an interferometer, comprising:
   at least one air portion whose total length is $x_{air}$;
   at least one known component, the at least one known component being necessary for production of an output signal from the reference arm when in use; and
   a glass portion having a length $x_{glass}$ and composed of a single glass type;
   wherein the length of the air portion, the length of the glass portion, and the single glass type are determined by balancing the group delay and the group dispersion delay (GDD) of an object arm of the interferometer with the group delay and the GDD of the reference arm.

6. The reference arm of claim 5 wherein balancing the GDD of each arm comprises setting $$x_{glass} \cdot \beta_{glass,2} + \Phi_{known,2} = \Phi_{obj,2},$$

where $x_{glass}$ is the length of the glass portion, $\beta_{glass,2}$ is the second derivative of the propagation constant of the glass portion with respect to frequency, $\Phi_{known,2}$ is the total GDD of the at least one known component, and $\Phi_{obj,2}$ is the GDD of the object arm, and wherein balancing the group delay of each arm comprises setting $$x_{air}/c + x_{glass} \cdot \beta_{glass,1} + \Phi_{known,1} = \Phi_{obj,1},$$

where $x_{air}$ is the length of the air portion, c is the speed of light in a vacuum, $\beta_{glass,1}$ is the first derivative of the propagation constant of the glass portion with respect to frequency, $\Phi_{known,1}$ is the total group delay of the at least one known component, and $\Phi_{obj,1}$ is the group delay of the object arm.

7. An optical coherence tomography (OCT) interferometer comprising:
an object arm having dispersive properties such that the group delay of an electromagnetic wave passing through the object arm has a group delay of $\Phi_{obj,1}$ and a group dispersion delay (GDD) of $\Phi_{obj,2}$; and
a reference arm comprising at least one air portion whose total length is $x_{air}$, at least one known component, the at least one known component being necessary for production of an output signal from the reference arm when in use, and a single glass portion with a length $x_{glass}$ and composed of glass of a single glass type.

8. The OCT interferometer of claim 7 wherein the length $x_{air}$ of the air portion, the length $x_{glass}$ of the glass portion, and the glass type are determined by balancing the group delay of the reference arm with the group delay $\Phi_{obj,1}$ of the object arm and balancing the GDD of the reference arm with the GDD $\Phi_{obj,2}$ of the object arm.

9. The OCT interferometer of claim 8 wherein balancing the GDD of each arm comprises setting $$x_{glass} \cdot \beta_{glass,2} + \Phi_{known,2} = \Phi_{obj,2},$$

where $\beta_{glass,2}$ is the second derivative of the propagation constant of the glass portion with respect to frequency and $\Phi_{known,2}$ is the total GDD of the at least one known component, and wherein balancing the group delay of each arm comprises setting $$x_{air}/c + x_{glass} \cdot \beta_{glass,1} + \Phi_{known,1} = \Phi_{obj,1},$$

where c is the speed of light in a vacuum, $\beta_{glass,1}$ is the first derivative of the propagation constant of the glass portion with respect to frequency, and $\Phi_{known,1}$ is the total group delay of the at least one known component.

* * * * *